(12) United States Patent
Wang et al.

(10) Patent No.: US 8,450,292 B2
(45) Date of Patent: May 28, 2013

(54) OLIGONUCLEOTIDES OR THEIR FUNCTIONAL HOMOLOGUES, A COMPOSITION COMPRISING THE SAME AND A METHOD OF TREATING B CELL NEOPLASM

(75) Inventors: Li-Ying Wang, Beijing (CN); Mu-sheng Bao, Beijing (CN); Yong-li Yu, Beijing (CN)

(73) Assignee: Changchun Huapu Biotechnology Co., Ltd. (CN)

( * ) Notice: Subject to any disclaimer, the term of this patent is extended or adjusted under 35 U.S.C. 154(b) by 0 days.

(21) Appl. No.: 13/310,595

(22) Filed: Dec. 2, 2011

(65) Prior Publication Data

US 2012/0142761 A1    Jun. 7, 2012

Related U.S. Application Data

(62) Division of application No. 11/914,744, filed as application No. PCT/CN2006/000215 on Feb. 13, 2006, now abandoned.

(30) Foreign Application Priority Data

May 17, 2005   (CN) .......................... 2005 1 0069576

(51) Int. Cl.
*A61K 31/70*   (2006.01)
*C07H 21/02*   (2006.01)

(52) U.S. Cl.
USPC ......... 514/44 A; 514/44 R; 435/375; 435/377

(58) Field of Classification Search
None
See application file for complete search history.

(56) References Cited

U.S. PATENT DOCUMENTS

| 6,896,885 B2 | 4/2005 | Hanna |
| 7,491,706 B2 | 2/2009 | Yu et al. |
| 7,576,066 B2 | 8/2009 | Krieg |

FOREIGN PATENT DOCUMENTS

| CN | 1526718 A | 9/2004 |
| CN | 1526719 A | 9/2004 |
| WO | WO 0122972 | 4/2001 |
| WO | WO 0197843 | 12/2001 |
| WO | WO 03030832 A2 | 4/2003 |
| WO | WO 03050241 A2 | 6/2003 |
| WO | WO 2004054657 | 7/2004 |
| WO | WO 2005014611 | 2/2005 |

OTHER PUBLICATIONS

Banchereau, J. et al., Annual Rev. Immunology, "The CD40 Antigen and its Ligand", 1994, vol. 12; pp. 881-992.
Castle, B. E. et al., J. Immunology, "Regulation of Expression of the Ligand for CD40 on T Helper Lymphocytes", Aug. 15, 1993, vol. 151; pp. 1777-1788.
Chen, et al., "Study of Antileukemic Effect of CpG-Oligodexynucleotides treated cord blood", Chin. J. Hematol, Jan. 2004, vol. 25, No. 1; pp. 13-16.
Chu, P. et al., PNAS, "Latent Sensitivity to Fas-mediated Apoptosis after CD40 Ligation may explain acivity of CD154 Gene Therapy in Chronic Lymphocytic leukemia", Mar. 19, 2002, vol. 99, No. 6; pp. 3854-3859.
Dalpke A.H. et al., "Immunostimulatory CpG-DNA Activates Murine Microglia." The Journal of Immunology, 2002, vol. 168; pp. 4854-4863.
D'Amico, G. et al., "CD40 Activation of BCP-ALL cells Generated IL-10 Producing, IL-12-defective APCs that Induce Allogenetic T-cell Anergy", Immunobiology Blood, vol. 104, No. 3, Aug. 1, 2004.
Decker, et al., "Sensitization of B-Cell Chronic Lymphocytic Leukemia Cells to Recombinant Immunotoxin by Immunostimulatory Phosphorothioate Oligodeoxynucleotides" Blood, vol. 99, No. 3, pp. 1320-1326, Feb. 15, 2002.
Decker, et al., "Immunostimulatory CpG-Oligonucleotides cause Proliferation, Cytokine Production, and an Immunogenic Phenotype in Chronic Lymphocytic Leukemia B cells", Blood, Feb. 1, 2000, vol. 95, No. 3; pp. 999-1006.
Dicker, F. et al., Blood, "Fas-ligand (CD178) and TRAIL Synergistically Induce Apoptosis of CD40-Activated Chronic Lymphocytic Leukemia B Cells" Apr. 15, 2005, vol. 105, No. 8; pp. 3193-3198.
Dilloo, D. et al., Blood, "CD40 Ligand Induces an Antileukemia Immune Response In Vivo" 1997, vol. 90; pp. 1927-1933.
Hartmann, G., et al., "Delineation of CpG Phosphorothioate Oligodeoxynucleotide for Activating Primate Immune Response In Vitro and In Vivo." Journal of Immunology, 2000, vol. 164; pp. 1617-1624.
Jahrsdörder, B., et al., "B-Cell Lymphomas Differ in their Responsiveness to CpG Oligodeoxynucleotides." Clinical Cancer Research, vol. II, pp. 1490-1499, Feb. 15, 2005.
Kamstrup, S. et al., "Response of Porcine Peripheral Blood Mononuclear Cells to CpG-containing Oligodeoxynucleotides." Vet. Microbiol., Feb. 26, 2001, vol. 78, No. 4; pp. 352-362.
Khanna, R. et al., J. Immunology, "Cutting Edge: Engagement of CD40 Antigen with Soluble CD40 Ligand Up Regulates Peptide Transporter Expression and Restores Endogenous Processing Function in Burkitt's Lymphoma Cells", 1997, vol. 159; pp. 5782-5785.
Kato, K. et al., J. Clin Invest., "Gene Transfer of CD40-Ligand Induces Autologous Immune Recognition of Chronic Lymphocytic Leukemia B Cells", Mar. 1998, vol. 101, No. 5; pp. 1133-1141.

(Continued)

*Primary Examiner* — Sean McGarry
(74) *Attorney, Agent, or Firm* — Morgan, Lewis & Bockius LLP

(57) ABSTRACT

The invention provides nine oligonuleotides with sequences of SEQ ID NO:1-9 or their functional homologues or a composition comprising the same and a method for treating B cell neoplasm by using the oligonuleotides or their functional homologues or the composition comprising the oligonuleotides. The oligonuleotides induce the apoptosis of B cell neoplastic cells, up-regulate CD40 on B cell neoplastic cells and stimulate the production of IL-10 from B cell neoplastic cells.

15 Claims, 3 Drawing Sheets

OTHER PUBLICATIONS

Li, J., et al, "CpG in the Immunothereapy of B Cell Lymphoma in an Animal Model", Journal of Immunotherapy, vol. 27, No. 6, p. S60, Nov. 2004.

Mocellin, S. et al., "Interleukin-10 and the Immune Response against Cancer: a Counterpoint." Journal of Leukocyte Biology. 2005, Vol, 78; pp. 1043-1051.

Ranheim, E.A. et al. J. Exp Med, "Activated T Cells Induce Expressions of B7/BB1 on Normal or Leukemic B Cells through a CD40-dependent Signal", Apr. 1993 vol. 177; pp. 925-935.

Reid, G.S., et al., "CpG Stimulation of Precursor B-lineage Acute Lymphoblastic Leukemia Induces a Distinct Change in Costimulatory Molecule Expression and Shifts Allogeneic T cells towards a Th 1 Response", Blood, May 1, 2005, vol. 105, No. 9; pp. 3641-3646.

Takahashi, S., et al., Hum Gene Ther., "Autologous Antileukemic Immune Response Induced by Chronic Lymphocytic Leukemia B Cells Expressing the CD40 Ligand and Interleukin 2 Transgene", Apr. 10, 2001, vol. 12; pp. 659-670.

Takahashi, S. et al., Cancer Gene Ther., "Transgenic Expression of CD40L and interleukin-2 Induces an Autologous Antitumor Immune Response in Patients with non-Hodgkin's Lymphoma", 2001, vol. 8, No. 5; pp. 378-387.

Tokunaga, T. "Anti-tumor Activity of Deoxyribonucleic Acid Fraction from Mycobacterium bovis BCG.I. Isolation, Physicochemical Characterization and Anti-Tumor Activity" JNCI, 1984, vol. 72; p. 955.

Viet Hornung, et al., "Quantitative Expression of Toll-Like Receptor 1-10 mRNA in Cellular Subsets of Human Peripheral Blood Mononuclear Cells and Sensitivity to CpG Oligodeoxynucleotide." The Journal of Immunology, 2002, vol. 168; pp. 4531-4537.

von Bergwelt Baildon, M.S., et al., Blood, "Human Primary and Memory Cytotoxic T Lymphocyte Response are Efficiently Induced by means of CD40-activated B cells as Antigens-presenting cells: Potential for clinical application", May 1, 2002, vol. 99, No. 9; pp. 3319-3325.

Warren, T. L., et al. "Synergism between Cytosine-Guanine Oligodeoxynucleotides and Monoclonal Antibody in the Treatment of Lymphoma." Seminars in Oncology, vol. 29, No. I, Suppl. 2; pp. 93-97, Feb. 2002.

Weiner, G. J. "The Immunobiology and Clinical Potential of Immunostimulatory CpG Oligodeoxynucleotides" J. Leukoc Biol., Oct. 2000, vol. 68; pp. 455-463.

Wierda, W. G., et al., Blood, "CD40-ligand (CD154) Gene Therapy for Crhonic Lymphocytic Leukemia", Nov. 1, 2000, vol. 96; pp. 2917-2924.

Yellin, M. J., et al., J. Immunol, "T Lymphocyte T Cell-B Cell-Activating Molecule/CD40-L Molecules Induce Normal B Cells or Chronic Lymphocytic Leukemia B Cells to Express CD80 (87/BB-1) and Enhance Their Costimulatory Activity", 1994, vol. 153; pp. 666-674.

OLIGONUCLEOTIDES OR THEIR FUNCTIONAL HOMOLOGUES, A COMPOSITION COMPRISING THE SAME AND A METHOD OF TREATING B CELL NEOPLASM

CROSS-REFERENCES TO RELATED APPLICATIONS

This present application is a Divisional of U.S. patent application Ser. No. 11/914,744, filed on Aug. 8, 2008, which is a U.S. National Phase Patent Application of of PCT Patent Application No. PCT/CN06/000215 filed Feb. 13, 2006 and claims priority to Chinese Patent Application 200510069576.4 filed on May 17, 2005, each of which is incorporated herein by reference in its entirety for all purposes.

TECHNICAL FIELD

The present invention provides nine oligonucleotides with the sequences as shown in SEQ ID NO:1 to 9, or their functional homologues, a composition comprising the same and a method for treating B-cell neoplasm using the oligonucleotides by inducing apoptosis of B cell neoplastic cells, up-regulating CD40 on B cell neoplastic cells and by stimulating B cell neoplastic cells to produce IL-10. The oligonucleotides or their functional homologues can be used individually or together, or be used in combination with chemotherapeutics, immunotherapeutics and radiation to treat B cell neoplasm.

BACKGROUND

Based WHO classification system (American Journal of Surgical Pathology, 1997, 21(1): 114-121), lymphoid malignancies are grouped into three major classes: B-cell neoplasm, T-cell/natural killer (NK)-cell neoplasm and Hodgkin's lymphomas.

The B-cell neoplasm is further divided into two groups: precursor B-cell neoplasm and peripheral B-cell neoplasm. Precursor B-cell neoplasm includes precursor B-acute lymphoblastic leukemia (B cell-acute lymphoblastic leukemia, B-ALL)/lymphoblastic lymphoma (LBL). Peripheral B-cell neoplasm includes B-cell chronic lymphocytic leukemia (B-CLL), small lymphocytic lymphoma, B-cell prolymphocytic leukemia, lympho plasmacytic lymphoma/immunocytoma, Mantle cell lymphoma, Follicular lymphoma, cutaneous follicular lymphoma, extranodal marginal zone B-cell lymphoma of MALT type, nodal marginal zone B-cell lymphoma (+/−monocytoid B-cells), splenic marginal zone lymphoma (+/−villous lymphocytes), hairy cell leukemia, plasmacytoma/plasma cell myeloma, diffuse large B-cell lymphoma, mediastinal (thymic) large B cell lymphoma, intravascular large B-cell lymphoma, primary effusion lymphoma and Burkitt's lymphoma.

B-cell chronic lymphocytic leukemia (B-CLL) and B cell-acute lymphoblastic/lymphocytic leukemia (B-ALL) are two types of B cell leukemia. The B-CLL cells express CD19, CD5 and CD23 (Nicholas Chiorazzi, M. D., et al. N Engl J Med 2005; 352:804-15). The B-ALL cells express CD19 and CD10 markers.

Small lymphocytic lymphoma is a B cell neoplasm. The small lymphocytic lymphoma cells express CD19, CD5 and CD23 (Catherine Thieblemont, et al. Blood. 2004; 103:2727-2737).

Depending on the B-cell neoplasm diagnosed, current treatment options are chemotherapy, radiotherapy and immunotherapy.

CD40, expressed on the cell surface of normal B lymphocytes and dentritic cells, is a member of tumor necrosis factor receptor (TNFR) family. CD40L (CD154), expressed on T lymohocytes, is a member of tumor necrosis factor family (Castle B E, et al. J Immunol 1993; 151: 1777-1788). Interaction of CD40L and CD40 promotes the proliferation, differentiation and antigen presentation of B lymphocytes, dendritic cells and monocytes (Ranheim E A, et al. J Exp Med 1993; 177: 925-935 Yellin M J, et al. J Immunol 1994; 153: 666-674; Banchereau J, et al. Annu Rev Immunol 1994; 12: 881-922; M. von Bergwelt-Baildon M S, et al. Blood 2002; 99: 3319-3325).

CD40 also expresses on the B cell neoplastic cells. It has been demonstrated that enhancing the CD40 expression promotes the apoptosis of B cell neoplastic cells (Peter Chu, et al. PNAS, Mar. 19, 2002, vol. 99, no: 6 3854-3859; Frank Dicker, et al. BLOOD, 15 Apr. 2005 Volume 105, Number 8: 3193-3198).

Both in vitro and in vivo experiments indicated that stimulation and up-regulation of CD40 induced growth inhibition of B-cell neoplastic cells (Funakoshi et al., Blood 83: 2787-2794, 1994; Murphy et al., Blood 86: 1946-1953, 1995; Eliopoulos, A. G., et al. 1996. Oncogene 13:2243; Hirano, A., et al. 1999. Blood 93:2999; Tong, A. W., M et al. 2001. Clin. Cancer Res. 7:691).

Promoting CD40 expression on B cell neoplastic cells was reported to enhance the antigenicity of B cell neoplastic cells and consequently fostered the generation of cytotoxic T lymphocyte (CTL) specific to the cells. The CTL can efficiently kill B cell neoplastic cells (Dilloo D, et al. Blood. 1997; 90:1927-1933; Kato K, et al. J Clin Invest. 1998; 101:1133-1141; Wierda W G, et al. Blood. 2000; 96:2917-2924; Takahashi S, et al. Hum Gene Ther. 2001; 12:659-670; Takahashi S, et al. Cancer Gene Ther. 2001; 8:378-387). In the presence of CD40L, CD40 expressing B cell chronic lymphocytic leukemia cells can be killed by CD4 cytotoxic T lymphocytes (Frank Dicker, et al. Blood, 15 Apr. 2005 Vol 105, Num 8: 3193-3198). Interaction of D40L and CD40 on cells of Burkett's lymphoma could promote the cell to present tumor antigens to specific CTLs (Khanna, R. et al. 1997. J. Immunol. 159:5782). In vivo experiments and clinical trials also demonstrated that activation of CD40 could enhance the immunogenicity of B cell chronic lymphocytic leukemia (B-CLL) cell and consequently induce the generation of CTLs specific to the cells (Kato, K., et al. 1998. J. Clin. Invest. 101:1133; Wierda, W. G., et al. 2000. Blood 96: 2917).

Together, these data indicate that enhancing CD40 expression on B cell neoplastic cells can stimulate the anti-tumor immunity against B cell neoplasm. The anti-tumor immunity includes but not limits to the following:
1. promoting the apoptosis of B cell neoplastic cells;
2. inhibiting the growth of B cell neoplastic cells;
3. enhancing the immunogenicity of B cell neoplastic cells and therefore fostering the generation of CTLs specific to the cells.

Interleukin-10 (IL-10) is a homodimer cytokine produced by certain T cell cells, monocytes, macrophages and some of neoplastic cells developed from B cells, T cells or NK cells (Kitabayashi et al., 1995; Masood et al., 1995; Sjoberg et al., 1996; Beatty et al., 1997; Boulland et al., 1998; Jones et al., 1999). IL-10 activity is mediated by its specific cell surface receptor expressed on antigen-presenting cells, lymphocytes B-cell and chronic lymphocytic leukemia (B-CLL) cells. It was found that addition of exogenous IL-10 inhibited the proliferation of B-CLL cells freshly isolated from patients (Jesper Jurlander, Chun-Fai Lai, Jimmy Tan, et al. Characterization of interleukin-10 receptor expression on B-cell chronic lymphocytic leukemia cells. Blood, Vol 89, No 11 (June 1), 1997: pp 4146-4152). IL-10 was also reported to inhibit the proliferation of B-CLL cells and enhance the apoptosis of B-CLL cells (Anne-Catherine Fluckiger, Isabelle Durand, and Jacques Banchereau. Interleukin 10 Induces Apoptotic Cell Death of B-Chronic Lymphocytic Leukemia Cells. J. Exp. Med. Volume 179 January 1994 91-99). Immunostimulating anticancer properties of IL-10 have been discussed in a review from which it is speculated that IL-10 over-expression within the tumor microenvironment may catalyze cancer immune rejection (Simone Mocellin, Francesco M. Marincola and Howard A. Young. Interleukin-10 and the immune response against cancer: a counterpoint. Journal of Leukocyte Biology. 2005; 78:1043-1051).

SUMMARY OF THE INVENTION

In the first embodiment, the present invention provides nine oligonucleotides also designated as Oligo1, Oligo3, Oligo4, Oligo5, Oligo6, Oligo7, Oligo8, Oligo9, Oligo10 with the sequences shown in SEQ ID NO1, 2, 3, 4, 5, 6, 7, 8, 9 respectively and their functional homologues. The oligonucleotides or their functional homologues can have a phosphate backbone modification that is a phosphorothioate or phosphorodithioate modification partial or complete. The oligonucleotides or their functional homologues can have chemical modifications or have substitutions with rare bases. The oligonucleotides or their functional homologues can be functional parts of any other DNA fragments or be cloned into a plasmid, bacterial vector, viral vector or DNA vaccine respectively. The oligonucleotides with the sequences of the SEQ ID NO:1-9 can be modified by adding one or more bases (preferable 1 to 10 bases) to their each end or by changing one to more bases in them. Those skilled in the art can determine to use the oligonucleotides with the sequences of SEQ ID NO:1-9 or their functional homologues individually or together, or to use DNA fragments comprising the oligonucleotides with the sequences (SEQ ID NO:1-9) respectively to achieve the object of the present invention based on the well-knowledge in the art and the teaching of the present invention.

In the second embodiment, the present invention provides a method for treatment of B cell neoplasm by using the oligonucleotides or their functional homologues of the present invention individually or together or by using the composition comprising the same in a subject. The subject is a human or animal. The B cell neoplasm includes but not limited to B cell leukemia, B cell lymphoma and myeloma.

In the third embodiment, the present invention provides a method for treating B cell neoplasm using the oligonucleotides or their functional homologues of the present invention individually or together or using the composition comprising the same by inducing the apoptosis of B cell neoplastic cells.

In the fourth embodiment, the present invention provides a method for treating B cell neoplasm using the oligonucleotides or their functional homologues of the present invention individually or together or using the composition comprising the same by up-regulating CD40 on B-cell neoplastic cells.

In the fifth embodiment, the present invention provides a method for treating B cell neoplasm using the oligonucleotides or their functional homologues of the present invention individually or together or using the composition comprising the same by stimulating B-cell neoplastic cells to produce IL-10.

In another embodiment, the present invention provides a composition comprising therapeutically effective amount of the oligonucleotides or their functional homologues of the present invention alone or in/with one or more pharmaceutically acceptable carriers. The composition is administered through enteral, parenteral and topical administration or by inhalation.

In yet another embodiment, the present invention provides a method for the treatment of B cell neoplasm, comprising administering a therapeutically effective amount of the oligonucleotides or their functional homologues of the present invention individually or together or a composition comprising the same or with at least one of anti-B cell neoplasm agents including chemotherapeutics, immunotherapeutics and the agents used in radiotherapy.

DETAILED DESCRIPTION OF THE INVENTION

Definitions

Figure 1:
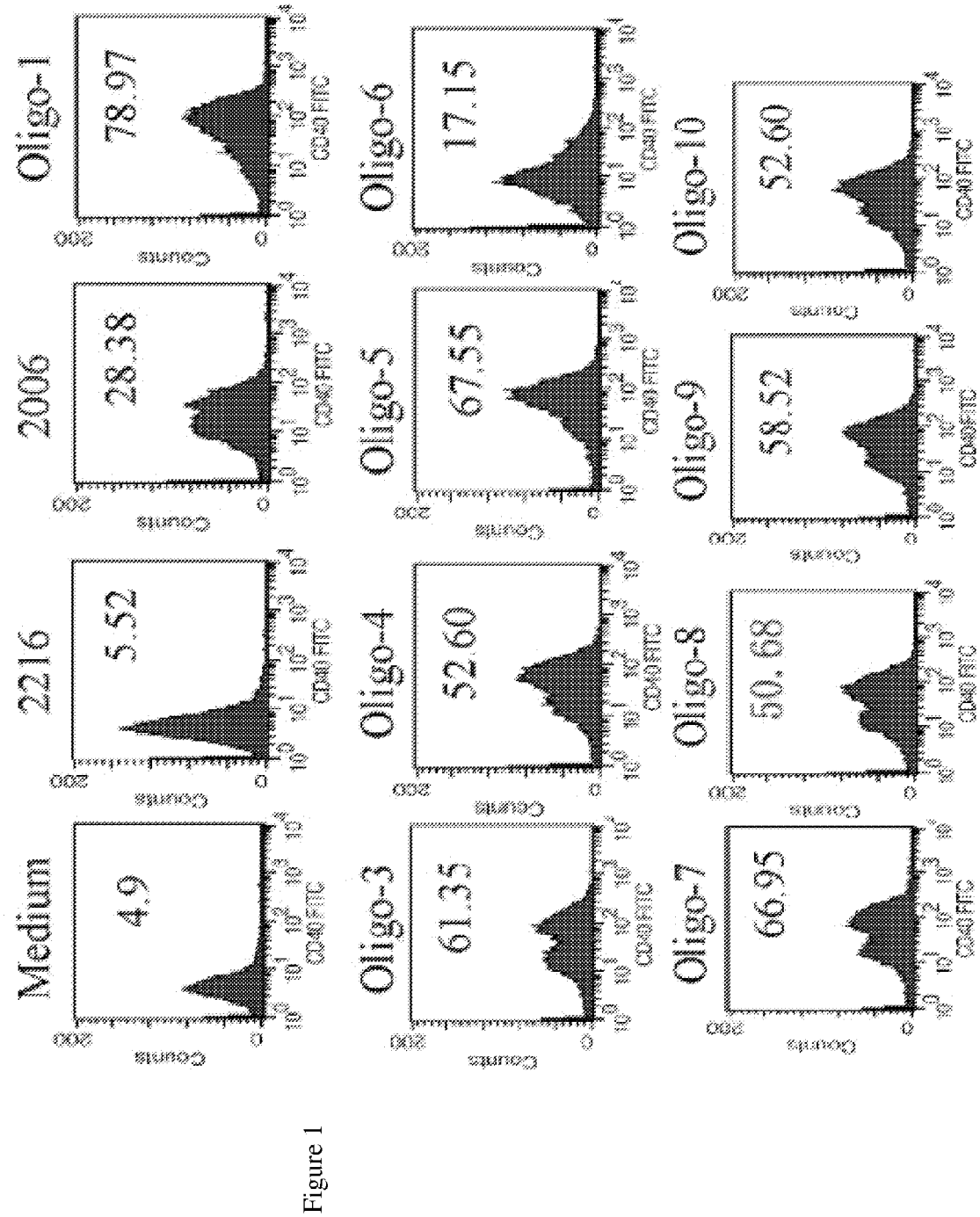
FIG. 1. The effect of the oligonucleotides on the up-regulation of CD40 on B-CLL cells The B-CLL cells were incubated with or without the oligonucleotides for 7 days and then were stained with FITC-CD40 antibody for analysis of CD40 expression using flow cytometry. The expression level was indicated with MFI number.

In the present invention, the following terms shall have the meanings below:

An "oligonucleotide" means multiple nucleotides (i.e. molecules comprising a sugar (e.g. deoxyribose) linked to a phosphate group and to an exchangeable organic base). There are four organic bases cytosine (C), thymine (T), adenine (A) and guanine (G). The oligonucleotide can be synthesized by an automated oligonucleotide synthesizer available in the market or be prepared from existing nucleic acid sequences using known techniques.

A "back bone modification" of oligonucleotide shall mean that an oligonucleotide can have a phosphorothioate modified phosphate backbone (i.e. at least one of the oxygens of the phosphate is replaced by sulfur) or other modified backbone.

A "chemical modification" of oligonucleotide shall mean the modification by utilizing the active groups of the nucleotide or creating nucleotide analogues. The modifications can occur either during or after synthesis of the oligonucleotide. During the synthesis, modified bases (including but not limited to Thymidine analogues) can be incorporated internally or on the 5' end. After the synthesis, the modification can be carried out using the active groups (via an amino modifier, via the 3' or 5' hydroxyl groups, or via the phosphate group).

A "B cell neoplasm" shall mean diseases developed from the abnormal proliferation of the cells of B lymphocyte lineage. The B cell neoplasm can be grouped into B cell leukemia, B cell lymphoma and myeloma (plasmacytoma/plasma cell myeloma). B cell leukemia includes B-cell chronic lymphocytic leukemia (B-CLL), precursor B-acute lymphoblastic leukemia (B cell acute lymphocytic leukemia, B-ALL), B-cell prolymphocytic leukemia and hairy cell leukemia. B cell lymphoma includes small lymphocytic lymphoma, lympho plasmacytic lymphoma/immunocytoma, Mantle cell lymphoma, Follicular lymphoma, cutaneous follicular lymphoma, extranodal marginal zone B-cell lymphoma of MALT type, nodal marginal zone B-cell lymphoma (+/−monocytoid B-cells), splenic marginal zone lymphoma (+/−villous lymphocytes), diffuse large B-cell lymphoma, mediastinal (thymic) large B cell lymphoma, intravascular large B-cell lymphoma, primary effusion lymphoma and Burkitt's lymphoma.

A "subject" shall mean a mammal including but not limited to human, monkey, dog, cat, horse, cow, pig, goat, sheep, mouse and rat. The oligonucleotides of the present invention can be administered to a subject with B cell neoplasm.

An "anti-B cell neoplasm agent" shall mean a agent used to treat B cell neoplasm in a subject. The agent includes the oligonucleotides of the present invention, chemotherapeutics, immunotherapeutics and the agents used in radiotherapy. The oligonucleotides of the present invention can be administered prior to, along with or after administration of one or more other anti-B cell neoplasm agents to achieve synergistic effect in treating a B cell neoplasm.

The "chemotherapeutics" shall mean the chemotherapeutics that treat B cell neoplasm in combination with the oligonucleotides of the present invention. The oligonucleotides of the present invention can be used with one or more chemotherapeutics in the treatment of B cell neoplasm. The chemotherapeutics include, but not limited to alkylating agents such as cyclophosphamide or chlorambucil, vinca alkaloids (e.g., vincristine and vinblastine), procarbazine, methotrexate, prednisone, anthracycline, L-asparaginase, purine analogs (e.g., fludarabine monophosphate, 2-chlorodeoxyadenosine and pentostatin), cytosine, arabinoside, cisplatin, etoposide and ifosfamide. The oligonucleotides of the present invention can also be used with one or more chemotherapeutic combinations in the chemotherapy. The combinations include, but not limited to CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin), MACOP-B (methotrexate, doxorubicin, cyclophosphamide, vincristine, fixed dose prednisone, bleomycin and leucovorin), IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP (B) (cyclophosphamide, etoposide, procarbazine, prednisone and bleomycin), CAMP (lomustine, mitoxantrone, cytarabine and prednisone), CHOP plus bleomycin, methotrexate, procarbazine, nitrogen mustard, cytosine arabinoside and etoposide. MOPP (mechlethamine (nitrogen mustard), vincristine (Oncovin), procarbazine and prednisone), ABVD (e.g., adriamycin, bleomycin, vinblastine and dacarbazine), ChIVPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) and CAP (cyclophosphamide, doxorubicin and prednisone).

The "immunotherapeutics" shall mean the immunotherapeutics that treat B cell neoplasm in combination with the oligonucleotides of the present invention. The oligonucleotides of the present invention can be used with one or more immunotherapeutics in the treatment of B cell neoplasm. The immunotherapeutics include, but not limited to anti-CD20 antibodies. The CD20 antibody includes immunoglobulins and its fragments that are specifically reactive with a CD20 protein on cell surface of B cell neoplastic cells. CD20 antibodies can be polyclonal and monoclonal antibodies, chimeric antibodies, bi-specific antibodies and humanized antibodies. A "CD20" is a B-cell membrane protein (Tedder et al., Immunology Today 15: 450-454 (1994)) and is expressed on both normal and neoplastic B-cell (John C. Byrd, et al. J Clin Oncol 2001; 19: 2165-2170; Huhn D, et al. Blood 2001, 98: 1326-1331).

A "pharmaceutically acceptable carrier" denotes one or more solid or liquid filler, diluents or encapsulating substances that are suitable for administering the oligonucleotides of the present invention to a subject. The carrier can be organic, inorganic, natural or synthetic. The carrier includes any and all solutions, diluents, solvents, dispersion media, liposome, emulsions, coatings, antibacterial and anti-fungal agents, isotonic and absorption delaying agents, and any other carrier suitable for administering the oligonucleotides of the present invention and their use is well known in the art.

The "therapeutically effective amount" of the oligonucleotides of the present invention shall refer to a dose used to achieve a desired result of treating B cell neoplasm in a subject. The dose can be determined by standard techniques well known to those skilled in the art and can vary depending the factors including, but not limited to the size or/and overall health of the subject or the severity of the disease. Introduction of the oligonucleotides of the invention can be carried out as a single treatment or over a series of treatments. Subject doses of the oligonucleotides of the present invention for the administration range from about 1 μg to 100 mg per administration. However, doses for the treatment of B cell neoplasm may be used in a range of 10 to 1,000 times higher than the doses described above. The dosage regimen can be adjusted to provide the optimum therapeutic effect by those skilled in the art.

The "route" of administering the oligonucleotides of the present invention shall mean the enteral, parenteral and topical administration or inhalation. The term "enteral" as used herein includes oral, gastric, intestinal and rectal administration. The term "parenteral" includes intravenous, intraperitoneal, intramuscular, subcutaneous, rectal or vaginal administration. The term "topical" denotes the application of the oligonucleotides externally to the epidermis, to the buccal cavity and into the ear, eye and nose.

A "pharmaceutical composition" shall mean the composition containing an therapeutically effective amount of the oligonucleotides with or without a pharmaceutically acceptable carrier. The composition includes but not limited to aqueous or saline solutions, particles, aerosols, pellets, granules, powders, tablets, coated tablets, (micro) capsules, suppositories, syrups, emulsions, suspensions, creams, drops and other pharmaceutical compositions suitable for use in a variety of drug delivery systems. The compositions are suitable for injection, oral, buccal, rectal and vaginal use, inhalation and application in depot. In all cases, the composition must be sterile and stable under the conditions of manufacture and storage and preserved against the microbial contamination. For injection, the composition will include aqueous solutions or dispersions and powders for the extemporaneous preparation of injectable solutions or dispersion. "Powder" in this invention refers to a composition that contains finely dispersed solid particles containing the oligonucleotides. The powder may be formulated with other pharmaceutically accepted carriers (e.g., water, PBS, saline and other pharmaceutically accepted buffers) before use. The solutions can be prepared by incorporating the oligonucleotides in one or more appropriate solvents and other required ingredients. Dispersions can be prepared by incorporating the oligonucleotides into a vehicle, which contains a dispersion medium (e.g., glycerol, liquid polyethylene glycols and oils) and the other required ingredients. For oral administration, the composition will be formulated with edible carriers to form tablets, pills, dragees, capsules, liquids, gels, syrups, slurries, suspensions and the like. For buccal administration, the composition will be tablets or lozenges in conventional manner. For inhalation, the composition will be an aerosol spray from pressurized packs or a nebulizer or a dry powder and can be selected by one of skill in the art. The oligonucleotides may also be formulated as pharmaceutical acceptable compositions for rectal or vaginal applications and for depot application. The oligonucleotides in the composition can be used alone or in combination with one or more other agents including but not limited to chemotherapeutics, immunotherapeutics and a ligand recognized by a specific receptor or molecule of target cell. The oligonucleotides in combination with another agent can be separate compositions and used as the following: (1) the oligonucleotides are mixed with a second agent before administration; (2) the oligonucleotides and a second agent are administered to a subject at different times; (3) the oligonucleotides and a second agent are administered to different sites of a subject. In addition, the composition may contain plasmid, bacterial vectors, viral vectors and nucleic acid vaccines carrying the sequence of the oligonucleotides of the present invention.

EXAMPLES

The following examples are illustrative, and should not be viewed as limiting the scope of the present invention. Reasonable variations, such as those occur to reasonable artisan, can be made herein without departing from the scope of the present invention.

Example 1

Synthesis of the Oligonucleotide

We have designed and synthesized the oligonucleotides with the following sequences and the nomenclatures:

```
Oligo 1:
                 (indicated in the SEQ ID NO: 1)
5'-TCgACgTTCgTCgTTCgTCgTTC-3'

Oligo 3:
                 (indicated in the SEQ ID NO: 2)
5'-TCggCACgCgACgTgCTggCCgTCgTTTCC-3'
```

```
Oligo 4:
                 (indicated in the SEQ ID NO: 3)
5'-TCgTCgTCgTCgTTgTCgTTgggg-3'

Oligo 5:
                 (indicated in the SEQ ID NO: 4)
5'-TCgTTgCCgTCgg-3'

Oligo 6:
                 (indicated in the SEQ ID NO: 5)
5'-TCgTCgggTgCgACgTCgCAgggggg-3'

Oligo 7:
                 (indicated in the SEQ ID NO: 6)
5'-TCgTCgggTgCgATCgCAgggggg-3'

Oligo 8
                 (indicated in the SEQ ID NO:)
5'-TCgTCgggTgCATCgATgCAgggggg-3'

Oligo 9:
                 (indicated in the SEQ ID NO: 8)
5'-tcgtcgggtgcgacgtcgca-3'

Oligo 10:
                 (indicated in the SEQ ID NO: 9)
5'-TCggggACgATCgTCgggggg-3'
```

To analyze the functions of the above Oligos, two control oligonucleotides of 2006 with the sequence of 5'-tcgtcgttttgtcgttttgtcgtt-3' and 2216 with the sequence of 5'-ggggggacgatcgtcgggggg-3' were also synthesized.

All of the oligonucleotides were synthesized in Sangon Biotech Company (Shanghai, China), tested for endotoxin by using the Limulus amebocyte lysate assay (Associates of Cape Cod, Inc) and manipulated in pyrogen-free reagents. 2006 (J Immunol 2000: 164: 1617) is a well studied oligonulceotide that strongly activates normal B cells. 2216 (Eur J Immunol 2001; 31:2154) is another well studied oligonuleotide that induces high amounts of type I interferon in plasmacytoid dendritic cells.

The methods for synthesizing the oligonucleotide are well known for those skilled in the art and among others, solid-phase synthesis is generally used. Specifically, in the process of the synthesis, the solid support used is controlled pore glass (CPG) bead. This bead has a surface with holes and channels and it is in these that the protected nucleotide is attached. The oligonucleotide synthesis begins with the 3'-most nucleotide and proceeds through a series of cycles composed of five steps that are repeated until the 5'-most nucleotide is attached. These steps are deprotection, activation, coupling, capping and stabilization.

Step 1. Deprotection

The protective group in the protected nucleoside attached to a CPG (controlled pore glass) bead is removed by trichloroacetic acid (TCA) leaving a reactive 5'-hydroxyl group.

Step 2. Activation

In this step, tetrazole attacks the coupling phosphoramidite nucleoside forming a tetrazolyl phosphoramidite intermediate.

Step 3. Coupling

The tetrazolyl phosphoramidite intermediate reacts with the hydroxyl group of the recipient and the 5' to 3' linkage is formed. The tetrazole is reconstituted and the process continues.

Step 4. Capping

In this step, an acetylating reagent composed of acetic anhydride and N-methyl imidazole is used to block the reactive hydroxyl group on its 5'-most end of the oligonucleotide to avoid of coupling failure.

Step 5. Stabilization

Once the capping step is accomplished, the last step in the cycle is oxidation which stabilizes the phosphate linkage between the growing oligonucleotide chain and the most recently added base. This step is carried out in the presence of Iodine as a mild oxidant in tetrahydrofuran (THF) and water.

Following this final step the cycle is repeated for each nucleotide in the sequence. After the completion of the synthesis, the single stranded DNA molecule is purified by methods such as HAP, PAGE, HPLC, C18 and OPC.

Example 2

Apoptosis of Human B-CLL Cells Induced by the Oligonucleotides

1. Preparation of Human B-CLL Cells

Blood samples from untreated B-CLL (pathologically identified) patients (The First Hospital, Jilin University, China) were drawn after obtaining written informed consent approved. Peripheral blood mononuclear cells (PBMCs) were isolated by Ficoll-Paque (Pharmacia) density gradient centrifugation. CD5+CD19+CD23+B-CLL cells in PBMCs were purified using B-cell isolation kit (Miltenyi Biotec, Bergisch Gladbach, Germany) to >95% of CD5+CD19+CD23+ cells (B-CLL cells). The cell preparation was performed under the guidance of Miltenyi Biotec.

2. Apoptosis of Human B-CLL Cells Induced by the Oligonucleotides

The B-CLL cells were incubated with Oligo1, Oligo3, Oligo4, Oligo5, Oligo6, Oligo7, Oligo8, Oligo9, Oligo10, 2006 or 2216 respectively at a final concentration of 3 µg/ml in 10% human AB serum RPMI 1640 medium (HyClone) at $10^6$ cells/well in a 48-well plate. The oligonucleotides were diluted in serum free RPMI 1640 medium (HyClone). An equal volume of the dilute (serum free RPMI 1640 medium (HyClone)) was used as a control (Medium).

On day 3, 5 and 7 after incubation, the cells were counted and stained with tetramethyl-rhodamine ethylester (TMRE) (Molecular Probes Inc)(Lena Thyrell, et al. The Journal of Biological Chemistry Vol. 279, No. 23, Issue of June 4, pp. 24152-24162, 2004) for 10 minutes. The TMRE positive (viable) and TMRE-negative (apoptotic) B-CLL cells were determined by flow cytometry (B.D. FACS Aria). Viable B-CLL cell number was calculated by multiplying total cell count with the TMRE-positive cell percentage at each time point. The experiment was repeated with ten blood samples from B-CLL patients and the averaged result (n=10) showed that the oligonucleotides significantly induced the apoptosis of B-CLL cells (Table-1).

TABLE 1

Apoptosis of B-CLL cells induced by the oligonucleotides
Viable B-cell chronic lymphocytic leukemia cells (%)
(n = 10)

| Groups | Time of Incubation (day) | | |
|---|---|---|---|
| | 3 | 5 | 7 |
| Oligo 1 | 55.7 | 27.7 | 19 |
| Oligo 3 | 85.5 | 37.3 | 31.6 |
| Oligo 4 | 60.1 | 38.8 | 27.5 |
| Oligo 5 | 58.1 | 38.1 | 23.2 |
| Oligo 6 | 52.3 | 34.9 | 31.7 |
| Oligo 7 | 59.6 | 38.4 | 30.2 |
| Oligo 8 | 51.1 | 34.2 | 29.6 |

TABLE 1-continued

Apoptosis of B-CLL cells induced by the oligonucleotides
Viable B-cell chronic lymphocytic leukemia cells (%)
(n = 10)

| Groups | Time of Incubation (day) | | |
|---|---|---|---|
| | 3 | 5 | 7 |
| Oligo 9 | 52.8 | 37.9 | 24.3 |
| Oligo 10 | 54.6 | 35.4 | 28.3 |
| Medium | 82.2 | 79.5 | 81.3 |
| 2006 | 66.5 | 44.4 | 40.2 |
| 2216 | 67.7 | 57.7 | 50.7 |

Example 3

Up-Regulation of CD40 on Human B-CLL Cells by the Oligonucleotides

1. Preparation of Human B-CLL Cells

Human B-CLL cells were isolated from B-CLL patients with the procedures as described as in example 2.

2. Up-Regulation of CD40 on Human B-CLL Cells by the Oligonucleotides

The B-CLL cells were incubated with Oligo1, Oligo3, Oligo4, Oligo5, Oligo6, Oligo7, Oligo8, Oligo9, Oligo10, 2006 or 2216 respectively at a final concentration of 3 µg/ml in 10% human AB serum RPMI 1640 medium (HyClone) at $10^6$ cells/well in a 48-well plate. The oligonulceotides were diluted in serum free RPMI 1640 medium (HyClone). An equal volume of the dilute (serum free RPMI 1640 medium (HyClone)) was used as a control (Medium).

On day 7 after the incubation, the cells were counted and stained with FITC-CD40 antibody (Becton ickinson) (Molecular Probes Inc)(Lena Thyrell, et al. The Journal of Biological Chemistry Vol. 279, No. 23, Issue of June 4, pp. 24152-24162, 2004) for 10 minutes. The CD40 antibody stained B-CLL cells were determined by flow cytometry (B.D. FACS Aria). The result (FIG. 1) showed that the oligonucleotides significantly up-regulate the expression of CD40 on B-CLL cells, indicating that the oligonucleotides can be used to treat B-CLL through the up-regulation of CD40 on the cells. The up-regulation of CD40 promotes the apoptosis of B-CLL cells, induces the growth inhibition of B-CLL cells and renders the B-CLL cells more immunogenic to stimulate the generation of CTLs specific to B-CLL cells. The experiment was repeated with at least ten blood samples from B-CLL patients with similar results.

Example 4

The Apoptosis of Human Small Lymphocytic Lymphoma Cells Induced by the Oligonucleotides 1. Preparation of Human Small Lymphocytic Lymphoma Cells The small lymphocytic lymphoma cells were isolated from the biopsy tissue of lymph node from patients (The First Hospital, Jilin University, China) with small lymphocytic lymphoma (pathologically identified) after obtaining written informed consent approved. The biopsy tissue was minced by rough surface glass slides to release the cells into 5 ml of 10% human AB serum RPMI 1640 medium (HyClone) in a 6 cm culture plate. The released cells were filtered through stainless steel mesh and collected into a 50 ml conical tube containing 15 ml serum free RPMI 1640 media. The tube was centrifuged at 300×g for 10 minutes and then the supernatant was discarded. CD5+CD19+CD23+ small lymphocytic lymphoma cells were purified using B-cell isolation kit (Miltenyi Biotec, Bergisch Gladbach, Germany) to >95% of CD5+CD19+CD23+cells (small lymphocytic lymphoma cells). The cell preparation was performed under the guidance of Miltenyi Biotec.

2. Apoptosis of Small Lymphocytic Lymphoma Cells Induced by the Oligonucleotides The small lymphocytic lymphoma cells were incubated with Oligo1, Oligo3, Oligo4, Oligo5, Oligo6, Oligo7, Oligo8, Oligo9, Oligo10, 2006 or 2216 respectively at a final concentration of 3 μg/ml in 10% human AB serum RPMI 1640 medium (HyClone) at $10^6$ cells/well in a 48-well plate. The oligonucleotides were diluted in serum free RPMI 1640 medium (HyClone). An equal volume of the dilute (serum free RPMI 1640 medium (HyClone)) was used as a control (Medium).

On day 3, 5 and 7 after the incubation, the cells were counted and stained with tetramethyl-rhodamine ethylester (TMRE) (Molecular Probes Inc)(Lena Thyrell, et al. THE JOURNAL OF BIOLOGICAL CHEMISTRY Vol. 279, No. 23, Issue of June 4, pp. 24152-24162, 2004) for 10 minutes. The TMRE positive (viable) and TMRE-negative (apoptotic) small lymphocytic lymphoma cells were determined by flow cytometry (B.D. FACS Aria). Viable small lymphocytic lymphoma cell number was calculated by multiplying total cell count with the TMRE-positive cell percentage at each time point. The experiment was repeated with five samples from the patients with small lymphocytic lymphoma and the averaged result (n=5) showed that the oligonucleotides significantly induce the apoptosis of the small lymphocytic lymphoma cells (Table-2), indicating that the oligonucleotides can be used to treat small lymphocytic lymphoma by inducing the apoptosis of the cells.

TABEL 2

Apoptosis of small lymphocytic lymphoma cells induced by the oligonucleotides
Viable small lymphocytic lymphoma cells (%)
(n = 5)

| Groups | Time of Incubation (day) | | |
|---|---|---|---|
| | 3 | 5 | 7 |
| Oligo 1 | 53.5 | 26.7 | 18 |
| Oligo 3 | 83.9 | 38.4 | 29.1 |
| Oligo 4 | 61.1 | 36.9 | 29.7 |
| Oligo 5 | 57.2 | 37.4 | 21.3 |
| Oligo 6 | 56.2 | 36.1 | 32.1 |
| Oligo 7 | 60.5 | 40.3 | 31.1 |
| Oligo 8 | 50.2 | 37.4 | 30.2 |
| Oligo 9 | 54.2 | 39.7 | 25.4 |
| Oligo 10 | 56.5 | 37.6 | 29.3 |
| Medium | 81.2 | 78.4 | 77.1 |
| 2006 | 67.6 | 45.3 | 41.1 |
| 2216 | 68.5 | 58.7 | 52.1 |

Example 5

Up-Regulation of CD40 of Small Lymphocytic Lymphoma Cells Induced by the Oligonucleotides 1. Preparation of Human Small Lymphocytic Lymphoma Cells Human small lymphocytic lymphoma cells were isolated from patients with the procedures as described in example 4.

2. Up-Regulation of CD40 of Small Lymphocytic Lymphoma Cells Induced by the Oligonucleotides The small lymphocytic lymphoma cells were incubated with Oligo1, Oligo3, Oligo4, Oligo5, Oligo6, Oligo7, Oligo8, Oligo9, Oligo10, 2006 or 2216 respectively at a final concentration of 3 μg/ml in 10% human AB serum RPMI 1640 medium (HyClone) at $10^6$ cells/well in a 48-well plate. The oligonucleotides were diluted in serum free RPMI 1640 medium (HyClone). An equal volume of the dilute (serum free RPMI 1640 medium (HyClone)) was used as a control (Medium).

Figure 2:
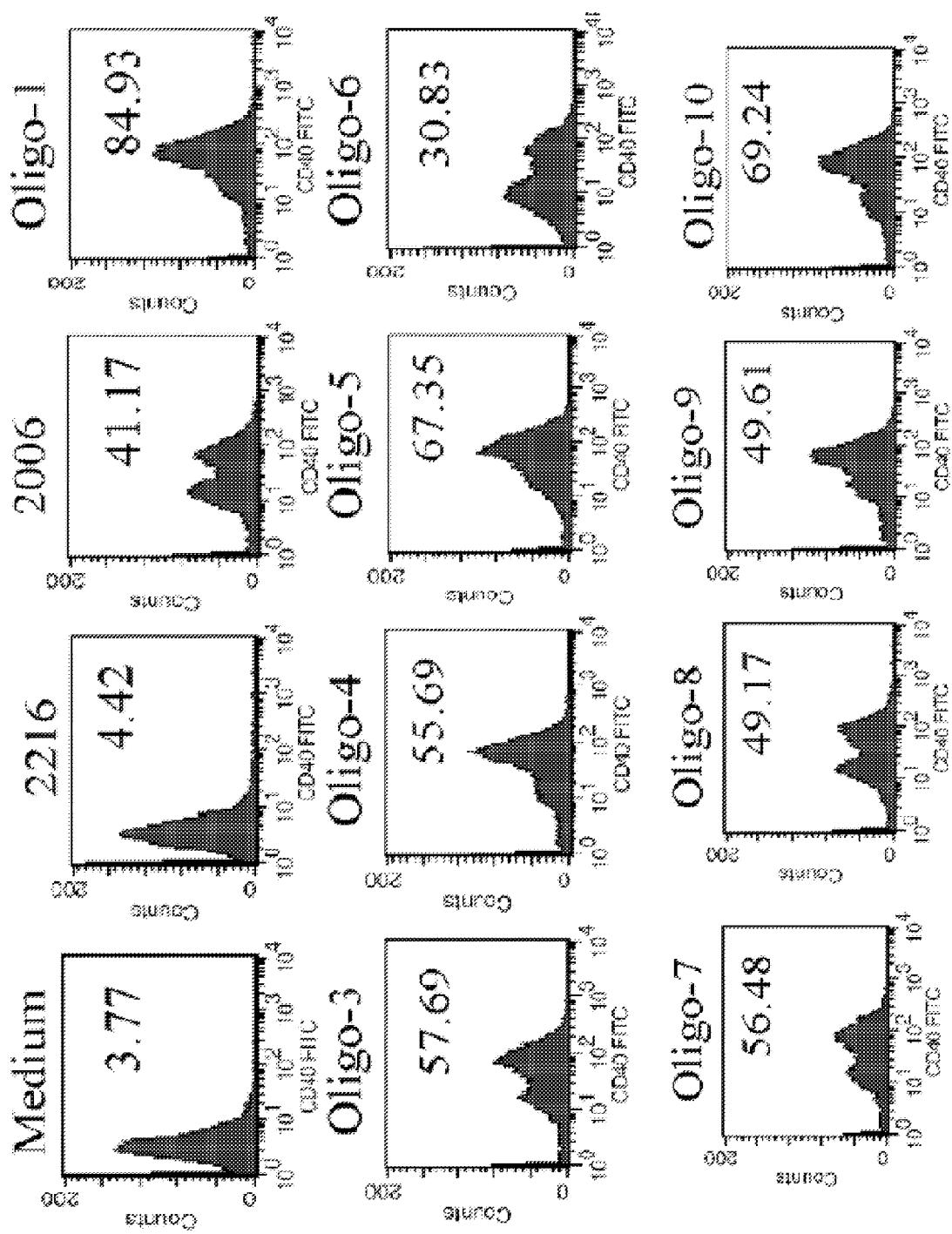
FIG. 2. The effect of oligonucleotides on the up-regulation of CD40 on small lymphocytic lymphoma cells The small lymphocytic lymphoma cells were incubated with or without the oligonucleotides. On day 7, the cells were stained with FITC-CD40 antibody for analysis of CD40 expression using flow cytometry. The expression level was indicated with MFI number.

On day 7 after the incubation, the cells were counted and stained with FITC-CD40 antibody (Becton ickinson) (Molecular Probes Inc)(Lena Thyrell. The Journal of Biological Chemistry Vol. 279, No. 23, Issue of June 4, pp. 24152-24162, 2004) for 10 minutes. The CD40 antibody stained small lymphocytic lymphoma cells were determined by flow cytometry (B.D. FACS Aria). The result (FIG. 2) showed that the oligonucleotides significantly up-regulate the expression of CD40 on small lymphocytic lymphoma cells, indicating that the oligonucleotides can be used to treat small lymphocytic lymphoma through the up-regulation of CD40 on the cells. The up-regulation of CD40 promotes the apoptosis of small lymphocytic lymphoma cells, induces the growth inhibition of small lymphocytic lymphoma cells and renders the small lymphocytic lymphoma cells more immunogenic to stimulate the generation of CTLs specific to small lymphocytic lymphoma cells. The experiment was repeated with five samples with similar results.

Example 6

Apoptosis of Human B-ALL Cells Induced by the Oligonucleotides

1. Preparation of Human B-ALL Cells

Blood samples from untreated B-ALL (pathologically identified) patients (The First Hospital, Jlin University, China) were drawn after obtaining written informed consent approved. PBMCs were isolated by Ficoll-Paque (Pharmacia) density gradient centrifugation. CD19+CD10+ B-ALL cells in PBMCs were purified using B-cell isolation kit (Miltenyi Biotec, Bergisch Gladbach, Germany) to >95% of CD19+CD10+ cells (B-ALL cells). The cell preparation was performed under the guidance of Miltenyi Biotec.

2. Apoptosis of B-ALL Cells Induced by the Oligonucleotides

The B-ALL cells were incubated with Oligo1, Oligo3, Oligo4, Oligo5, Oligo6, Oligo7, Oligo8, Oligo9, Oligo10, 2006 or 2216 respectively at a final concentration of 3 μg/ml in 10% human AB serum RPMI 1640 medium (HyClone) at $10^6$ cells/well in a 48-well plate. The oligonucleotides were diluted in serum free RPMI 1640 medium (HyClone). An equal volume of the dilute (serum free RPMI 1640 medium (HyClone)) was used as a control (Medium).

On day 3, 5 and 7 after the incubation, the cells were counted and stained with tetramethyl-rhodamine ethylester (TMRE) (Molecular Probes Inc)(Lena Thyrell, et al. The Journal of Biological Chemistry Vol. 279, No. 23, Issue of June 4, pp. 24152-24162, 2004) for 10 minutes. The TMRE positive (viable) and TMRE-negative (apoptotic) B-ALL cells were determined by flow cytometry (B.D. FACS Aria). Viable B-ALL cell number was calculated by multiplying total cell count with the TMRE-positive cell percentage at each time point. The experiment was performed with ten blood samples from B-ALL patients and the averaged result (n=10) showed that the oligonucleotides significantly induced the apoptosis of B-ALL cells (Table-3), demonstrating that the oligonucleotides can be used to treat B-ALL by inducing the apoptosis of B-ALL cells.

TABLE 3

The apoptosis of B-ALL cells induced by the oligonucleotides
Viable B-ALL cells (%) (n = 10)

| Groups | Time of Incubation (days) | | |
|---|---|---|---|
| | 3 | 5 | 7 |
| Oligo 1 | 66.9 | 60.1 | 59.5 |
| Oligo 3 | 67.9 | 64.1 | 65 |
| Oligo 4 | 69.2 | 66.2 | 65.7 |
| Oligo 5 | 70.6 | 68.2 | 67 |
| Oligo 6 | 66.4 | 61 | 60.3 |
| Oligo 7 | 75.9 | 70.1 | 69.2 |
| Oligo 8 | 80.1 | 74.9 | 72.3 |
| Oligo 9 | 67.2 | 63.1 | 62.9 |
| Oligo 10 | 72.6 | 68.1 | 65.3 |
| Medium | 91.5 | 92.7 | 93.1 |
| 2216 | 94.9 | 95 | 93.5 |
| 2006 | 62.9 | 58.4 | 59 |

Example 7

The Up-Regulation of CD40 on B-ALL Cells by the Oligonucleotides

1. Preparation of Human B-ALL Cells

Human B-ALL cells were prepared from the blood samples of patients with the procedures as described in example 6.

The B-ALL cells were incubated with or without the Oligo1, Oligo3, Oligo4, Oligo5, Oligo6, Oligo7, Oligo8, Oligo9, Oligo10, 2006 or 2216 respectively at a final concentration of 3 μg/ml in 10% human AB serum RPMI 1640 medium (HyClone) at $10^6$ cells/well in a 48-well plate. The oligonucleotides were diluted in serum free RPMI 1640 medium (HyClone). An equal volume of the dilute (serum free RPMI 1640 medium (HyClone)) was used as a control (Medium).

On day 3, 5, 7 after the incubation, the cells were counted and stained with FITC-CD40 antibody (Becton ickinson) (Molecular Probes Inc)(Lena Thyrell, et al. The Journal of Biological Chemistry Vol. 279, No. 23, Issue of June 4, pp. 24152-24162, 2004) for 10 minutes. The CD40 antibody stained small lymphocytic lymphoma cells were determined by flow cytometry (B.D. FACS Aria). The experiment was repeated with ten samples and the averaged result (Table-4) showed that the oligonucleotides significantly up-regulate the expression of CD40 on B-ALL cells, indicating that the oligonucleotides can be used to treat B-ALL by up-regulating CD40 on the cells. The up-regulation of CD40 promotes the apoptosis of B-ALL cells, induces the growth inhibition of B-ALL cells and renders the B-ALL cells more immunogenic to stimulate the generation of CTLs specific to B-ALL cells.

TABLE 4

Up-regulation of CD40 on B-ALL cells by the oligonucleotides
CD40 expression on B-cell acute lymphocytic
leukemia cells (MFI) (n = 10)

| Groups | Time of Incubation (days) | | |
|---|---|---|---|
| | 3 | 5 | 7 |
| Oligo 1 | 33.6 | 33.9 | 34.2 |
| Oligo 3 | 29.9 | 29.1 | 30.2 |
| Oligo 4 | 30.1 | 29.9 | 31.6 |
| Oligo 5 | 25.3 | 26.6 | 26.9 |
| Oligo 6 | 32.9 | 32.8 | 33.1 |
| Oligo 7 | 27.8 | 28.1 | 29.2 |
| Oligo 8 | 15.9 | 17.2 | 17.8 |
| Oligo 9 | 28.2 | 28.1 | 29.2 |
| Oligo 10 | 26.9 | 27.4 | 27.8 |
| Medium | 7.2 | 7.9 | 8.5 |
| 2216 | 9.9 | 9.5 | 10.6 |
| 2006 | 33.7 | 33.8 | 34.1 |

Example 8

The Production of IL-10 from B-CLL Induced by the Oligonucleotides

1. Preparation of human B-CLL cells

Human B-CLL cells were isolated from B-CLL patients with the procedures as described as in example 2.

2. The Production of IL-10 from B-CLL Induced by the Oligonucleotides

The B-CLL cells were culture with or without the Oligo1, Oligo3, Oligo4, Oligo5, Oligo6, Oligo7, Oligo8, Oligo9, Oligo10 respectively at a final concentration of 3 μg/ml in serum-free RPMI 1640 medium (HyClone) at $10^6$ cells/well in a 48-well plate in triplicates. The oligonuleotides were diluted in serum free RPMI 1640 medium (HyClone). An equal volume of the dilute (serum free RPMI 1640 medium (HyClone)) was used as a control (Medium).

The culture supernatants were collected at 24 h or the indicated time points and assessed for IL-10 in Fluorokine MAP Immunoarray (R&D Systems) system. Our data showed that triggering with the oligonucleotides led to the production of a high level of IL-10 from B-CLL cells (Table-5). In addition, our data further showed that adding exogenous rh-IL-10 (Schering Corp) into B-CLL cell cultures induced apoptotic B-CLL cells in an IL-10 dose-dependent manner, which could be specifically blocked by anti-IL-10 antibody (R & D Systems). These findings demonstrate that the oligonucleotides can be used to treat B-CLL by inducing the production of IL-10 that provokes the apoptosis of B-CLL cells in an autocrine manner. The experiment was repeated with at least ten samples from B-CLL patients with similar results.

TABLE 5

Interleukin-10 production from B-CLL cells induced
by the oligonucleotides
IL-10 production by B-CLL cells

| Group | pg/ml |
|---|---|
| Oligo 1 | 800 |
| Oligo 3 | 621 |
| Oligo 4 | 469 |
| Oligo 5 | 523 |
| Oligo 6 | 112 |

TABLE 5-continued

Interleukin-10 production from B-CLL cells induced
by the oligonucleotides
IL-10 production by B-CLL cells

| Group | pg/ml |
|---|---|
| Oligo 7 | 576 |
| Oligo 8 | 502 |
| Oligo 9 | 455 |
| Oligo 10 | 752 |
| Medium | 01.2 |

Example 9

The Effect of the Oligonucleotides on the Proliferation of Human Normal PBMC

Human PBMCs were isolated from buffy coats of normal blood donors (The Blood Center of Jilin Province, China) by Ficoll-Hypaque density gradient centrifugation (Pharmacia). The viability of the PBMCs was 95-99% as determined by trypan blue exclusion.

Figure 3:
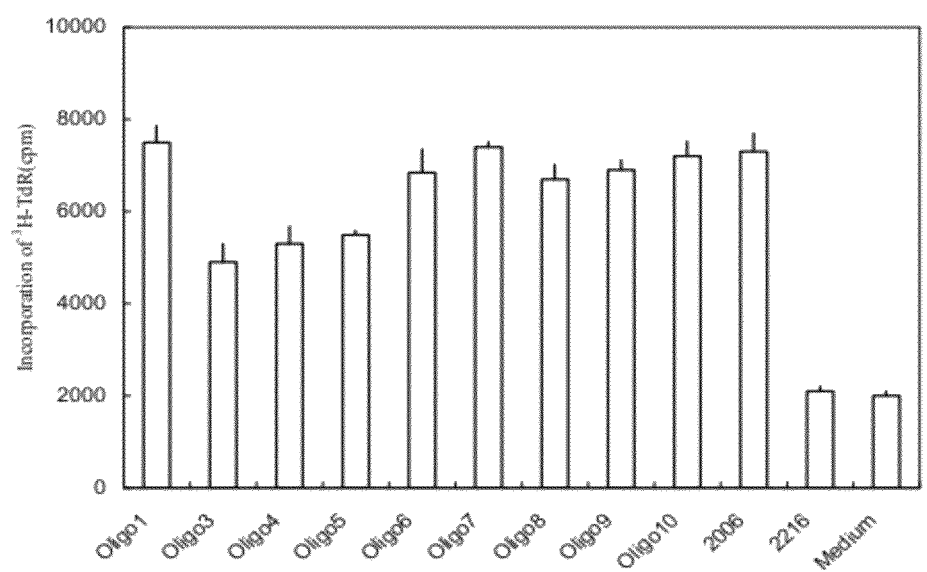
FIG. 3. The effect of the oligonucleotides on the proliferation of normal human PBMC The normal human PBMCs were cultured with or without the oligonucleotides and then incorporated with [$^3$H] thymidine for determining the proliferation of the cells. The proliferation of cells was expressed as cpm.

The PBMCs ($6 \times 10^5$/well) were plated in 96-well U-bottomed plates (Costar) and cultured with or without the Oligo1, Oligo3, Oligo4, Oligo5, Oligo6, Oligo7, Oligo8, Oligo9, Oligo10, 2006 or 2216 respectively at a final concentration of 6 μg/ml in triplicates for 36 h, followed by pulsing with [$^3$H] thymidine (New England Nuclear, Boston, Mass.) for 16 h. The cells were harvested on glass fiber filters and detected in a scintillation counter. The cell proliferation was expressed as cpm (counts per minute) (from triplet wells). Data from five normal blood samples are shown. 2006 and 2216 were used in controls. The results showed that the oligonucleotides could stimulate the PBMCs to proliferate obviously (FIG. 3), indicating that the oligonucleotides, instead of inducing the apoptosis, are proliferation-stimulatory to normal human PBMCs and isn't toxic to the cultured cells.

Having described the invention in detail and by reference to the preferred embodiments it will be apparent to those skilled in the art that modifications and variations are possible without departing from the scope of the invention as defined in the following appended claims.

We claim:

1. A method for treating B cell neoplasm in a mammalian subject, comprising administering to a subject in need of treating a therapeutically effective amount of a pharmaceutical composition comprising an oligonucleotide having the sequence of SEQ ID NO: 1.

2. The method according to claim 1, wherein said method comprising inducing apoptosis of B-cell neoplastic cells.

3. The method according to claim 1, wherein said method comprising up-regulating CD40 on B-cell neoplastic cells.

4. The method according to claim 1, wherein said method comprising stimulating B-cell neoplastic cells to produce IL-10.

5. The method according to claim 1, wherein said B cell neoplasm is B cell leukemia, B cell lymphoma or myeloma.

6. The method according to claim 5, wherein said B cell leukemia is B cell chronic lymphocytic leukemia or B cell acute lymphocytic leukemia.

7. The method according to claim 5, wherein said B cell lymphoma is small lymphocytic lymphoma.

8. The method according to claim 1, wherein said mammalian subject is a human subject.

9. The method according to claim 1, wherein said pharmaceutical composition is administered enterally, parenterally or topically or by inhalation.

10. A method of inducing apoptosis of B-cell neoplastic cells, comprising contacting said B-cell neoplastic cells with a composition comprising an oligonucleotide having the sequence of SEQ ID NO: 1.

11. A method for enhancing the expression of CD40 on B cell neoplastic cells, comprising contacting said B-cell neoplastic cells with a composition comprising an oligonucleotide having the sequence of SEQ ID NO: 1.

12. A method for inducing B cell neoplastic cells to produce IL-10, comprising contacting said B-cell neoplastic cells with a composition comprising an oligonucleotide having the sequence of SEQ ID NO: 1.

13. The method according to any one of claims 10-12, wherein said B-cell neoplastic cells are B-cell chronic lymphocytic leukemia (B-CLL) cells.

14. The method according to claim 10 or 11, wherein said B-cell neoplastic cells are B-cell acute lymphocytic leukemia (B-ALL) cells.

15. The method according to claim 10 or 11, wherein said B-cell neoplastic cells are small lymphocytics lymphoma cells.

* * * * *

SEQUENCE LISTING

<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: Oligo-1

<400> SEQUENCE: 1
tcgacgttcg tcgttcgtcg ttc                                     23

<210> SEQ ID NO 2
<211> LENGTH: 30
<212> TYPE: DNA
<213> ORGANISM: Artificial Sequence
<220> FEATURE:
<223> OTHER INFORMATION: Oligo-3

<400> SEQUENCE: 2
tcggcacgcg acgtgctggc cgtcgtttcc                              30

<210> SEQ ID NO 3
<211> LENGTH: 24
<212> TYPE: DNA
<213> ORGANISM: Artificial Sequence
<220> FEATURE:
<223> OTHER INFORMATION: Oligo-4

<400> SEQUENCE: 3
tcgtcgtcgt cgttgtcgtt gggg                                    24

<210> SEQ ID NO 4
<211> LENGTH: 13
<212> TYPE: DNA
<213> ORGANISM: Artificial Sequence
<220> FEATURE:
<223> OTHER INFORMATION: Oligo-5

<400> SEQUENCE: 4
tcgttgccgt cgg                                                13

-continued

```
<210> SEQ ID NO 5
<211> LENGTH: 26
<212> TYPE: DNA
<213> ORGANISM: Artificial Sequence
<220> FEATURE:
<223> OTHER INFORMATION: Oligo-6

<400> SEQUENCE: 5
tcgtcgggtg cgacgtcgca gggggg                                          26

<210> SEQ ID NO 6
<211> LENGTH: 24
<212> TYPE: DNA
<213> ORGANISM: Artificial Sequence
<220> FEATURE:
<223> OTHER INFORMATION: Oligo-7

<400> SEQUENCE: 6
tcgtcgggtg cgatcgcagg gggg                                            24

<210> SEQ ID NO 7
<211> LENGTH: 26
<212> TYPE: DNA
<213> ORGANISM: Artificial Sequence
<220> FEATURE:
<223> OTHER INFORMATION: Oligo-8

<400> SEQUENCE: 7
tcgtcgggtg catcgatgca gggggg                                          26

<210> SEQ ID NO 8
<211> LENGTH: 20
<212> TYPE: DNA
<213> ORGANISM: Artificial Sequence
<220> FEATURE:
<223> OTHER INFORMATION: Oligo-9

<400> SEQUENCE: 8
tcgtcgggtg cgacgtcgca                                                 20

<210> SEQ ID NO 9
<211> LENGTH: 21
<212> TYPE: DNA
<213> ORGANISM: Artificial Sequence
<220> FEATURE:
<223> OTHER INFORMATION: Oligo-10

<400> SEQUENCE: 9
tcggggacga tcgtcggggg g                                               21

<210> SEQ ID NO 10
<211> LENGTH: 24
<212> TYPE: DNA
<213> ORGANISM: Artificial Sequence
<220> FEATURE:
<223> OTHER INFORMATION: control oligonucleotide of 2006

<400> SEQUENCE: 10
tcgtcgtttt gtcgttttgt cgtt                                            24

<210> SEQ ID NO 11
<211> LENGTH: 20
<212> TYPE: DNA
<213> ORGANISM: Artificial Sequence
<220> FEATURE:
<223> OTHER INFORMATION: control oligonucleotide of 2216
```

```
<400> SEQUENCE: 11
gggggacgat cgtcggggggg                                              20
```